United States Patent
McKendrick et al.

(10) Patent No.: US 10,932,041 B2
(45) Date of Patent: Feb. 23, 2021

(54) METHOD OF DETECTING POTENTIAL MIGRAINE ONSET

(71) Applicants: The University of Melbourne, Melbourne (AU); The University of Western Australia, Crawley (AU)

(72) Inventors: Allison McKendrick, Melbourne (AU); David Badcock, Crawley (AU)

(73) Assignees: The University of Melbourne, Melbourne (AU); The University of Western Australia, Crawley (AU)

( * ) Notice: Subject to any disclaimer, the term of this patent is extended or adjusted under 35 U.S.C. 154(b) by 0 days.

(21) Appl. No.: 16/670,328

(22) Filed: Oct. 31, 2019

(65) Prior Publication Data

US 2020/0138384 A1 May 7, 2020

Related U.S. Application Data

(60) Provisional application No. 62/754,727, filed on Nov. 2, 2018.

(51) Int. Cl.
*H04R 3/00* (2006.01)
*A61B 5/00* (2006.01)
*H04R 1/40* (2006.01)
*H04L 12/18* (2006.01)

(52) U.S. Cl.
CPC ............ *H04R 3/005* (2013.01); *A61B 5/746* (2013.01); *H04L 12/1822* (2013.01); *H04R 1/406* (2013.01); *A61B 5/0022* (2013.01)

(58) Field of Classification Search
CPC ........................................................ A61B 5/00
See application file for complete search history.

(56) References Cited

U.S. PATENT DOCUMENTS 6,066,092 A * 5/2000 Cady .................... A61B 5/16
600/300

OTHER PUBLICATIONS

Hegarty, "Visual-Spacial Ability Test," 2010, Science Direct, The Psychology of Learning and Motivation, paragraphs 2.1 through 6.1 (no pages given) (Year: 2010).*
Stafford et al., "EQ-5D-derived utility values for different levels of migrane severity from a UK sample of migraineurs," 2012, Health and Quality of Life Outcomes, pp. 1-8 (Year: 2012).*

(Continued)

*Primary Examiner* — Nabil H Syed
*Assistant Examiner* — Cal J Eustaquio
(74) *Attorney, Agent, or Firm* — Marshall, Gerstein & Borun LLP (57) ABSTRACT

A method of outputting a warning indicative of potential migraine onset includes controlling a display of an electronic device to display, to a user, test stimuli of at least one spatial visual contextual test that is a perceptual analogue of centre-surround neuronal responses in human vision, and receiving, via an input device of the electronic device, at least one response of the user to the test stimuli. The method also includes processing the at least one response of the user to obtain test outcome data, and outputting a warning indication of potential migraine onset to the user if the test outcome data is outside an expected range for daily fluctuation in test outcome data.

8 Claims, 5 Drawing Sheets

(56) References Cited

OTHER PUBLICATIONS

Rapoport et al., "Remote electrical neuromodulatoin (REN) in the acute treatment of migraine: a comparison with usual care and acute migraine medications," The Journal of Headache and Pain. pp. 1-7. (Year: 2019).*

Spierlings et al., "Sufficiency and Necessity in Migraine: How do we Figure Out if Triggers are Absolute or Partial and, if Partial, Additive or Potentiating?" Curr Pain Headache Report, 2014. pp. 1-7 (Year: 2014).*

Peris et al., "Towards improved imigraine management: Determioning potential trigger factors in individual patients," Cephalalgia, An Intenational Journal of Headache, International Headache Society, 2017, vol. 37(5), 452-463. (Year: 2017).*

\* cited by examiner

METHOD OF DETECTING POTENTIAL MIGRAINE ONSET

RELATED APPLICATION

This application claims priority of U.S. provisional application 62/754,727 filed 2 Nov. 2018 and entitled "Method of Detecting Potential Migraine Onset", the disclosure of which is incorporated herein by reference for all purposes.

FIELD OF THE INVENTION

The invention relates to a method of outputting a warning indicative of potential migraine onset.

BACKGROUND

Migraine is a cyclic disorder including prodromal stages, attack, and recovery. Functional assessment of migraine patients at different stages of this cycle may contribute to a more comprehensive understanding of migraine, however there are logistical challenges involved, particularly in capturing the days immediately prior to a migraine. Techniques such as neuroimaging and electrophysiology are extremely useful for studying migraine pathophysiology, however they are costly and require specialised equipment. Because these tests are typically repeated at sporadic intervals within individuals, it is highly challenging to precisely define functional changes arising during the time course of a migraine event with such methods. Neuroimaging is also not suitable for all people due to issues with claustrophobia, metal implants, etc.

While migraines are a common neurological issue little is known of their cause nor how to treat more than the symptoms. Pain relief is used to manage the pain, but it can be debilitating enough to impact quality of life, preventing activities like work.

Current approaches to managing migraines are to avoid likely triggers, such as foods and food additives, sensory stimuli, changes in wake-sleep patterns, changes in weather, and medications. Some recording and management applications have been made to track exposure to triggers and to identify the ones which contribute to an individual's risk of migraine, however, none can provide advanced notice of the onset of a migraine.

There is a need for migraine sufferers to be able to perform self-testing that will provide advanced notice of onset of a migraine.

BRIEF SUMMARY

Embodiments of the invention relate to conducting visual testing to identify potential migraine onset using an electronic device. Suitable visual test stimuli include visual contextual tests that are a perceptual analogue of centre-surround neuronal responses in human vision.

An embodiment provides a method of outputting a warning indicative of potential migraine onset. The method comprises controlling a display of an electronic device to display, to a user, test stimuli of at least one spatial visual contextual test that is a perceptual analogue of centre-surround neuronal responses in human vision, receiving, via an input device of the electronic device, at least one response of the user to the test stimuli, processing the at least one response of the user to obtain test outcome data, and outputting a warning indication of potential migraine onset to the user if the test outcome data is outside an expected range for daily fluctuation in test outcome data.

BRIEF DESCRIPTION OF THE DRAWINGS

Embodiments of the disclosure are described in relation to the accompanying drawings in which.

DETAILED DESCRIPTION

Embodiments of the disclosure employ visual testing using an electronic device, such as a tablet device, in order to identify if the outcome of user's visual test is outside an expected range for daily fluctuation in test outcome data and using this as a basis to generate a warning indication to the user of the possible onset of a migraine. A warning, could, for example, enable a user to modify their behaviour in a way that would mitigate against the migraine developing, for example, by avoiding certain triggers or could enable the user to make contingency plans in respect of their potential debilitation by the migraine. Risk factors are highly individual, however, where a sufferer has known or suspected risk factors for migraine triggering, they may wish to take more care avoid these. These are typically factors such as fatigue, certain foods, more/less caffeine, stress, vigorous exercise etc. In addition to trying to mitigate a migraine eventuating, individuals might also wish to make back-up plans to reorganize life activities (e.g. make a back-up plan in case of feeling too unwell to pick up kids from school).

This advanced warning may also allow a user to pre-emptively take pain relief medication or undergo physical therapy. For example, if the prediction was highly accurate for an individual, they might want to (in consultation with their doctor) begin acute migraine pharmacotherapy for 24 hours to decrease attack severity/occurrence. It may also open new treatment approaches, allowing medication to be administered prior to the onset of the migraine.

Figure 5:
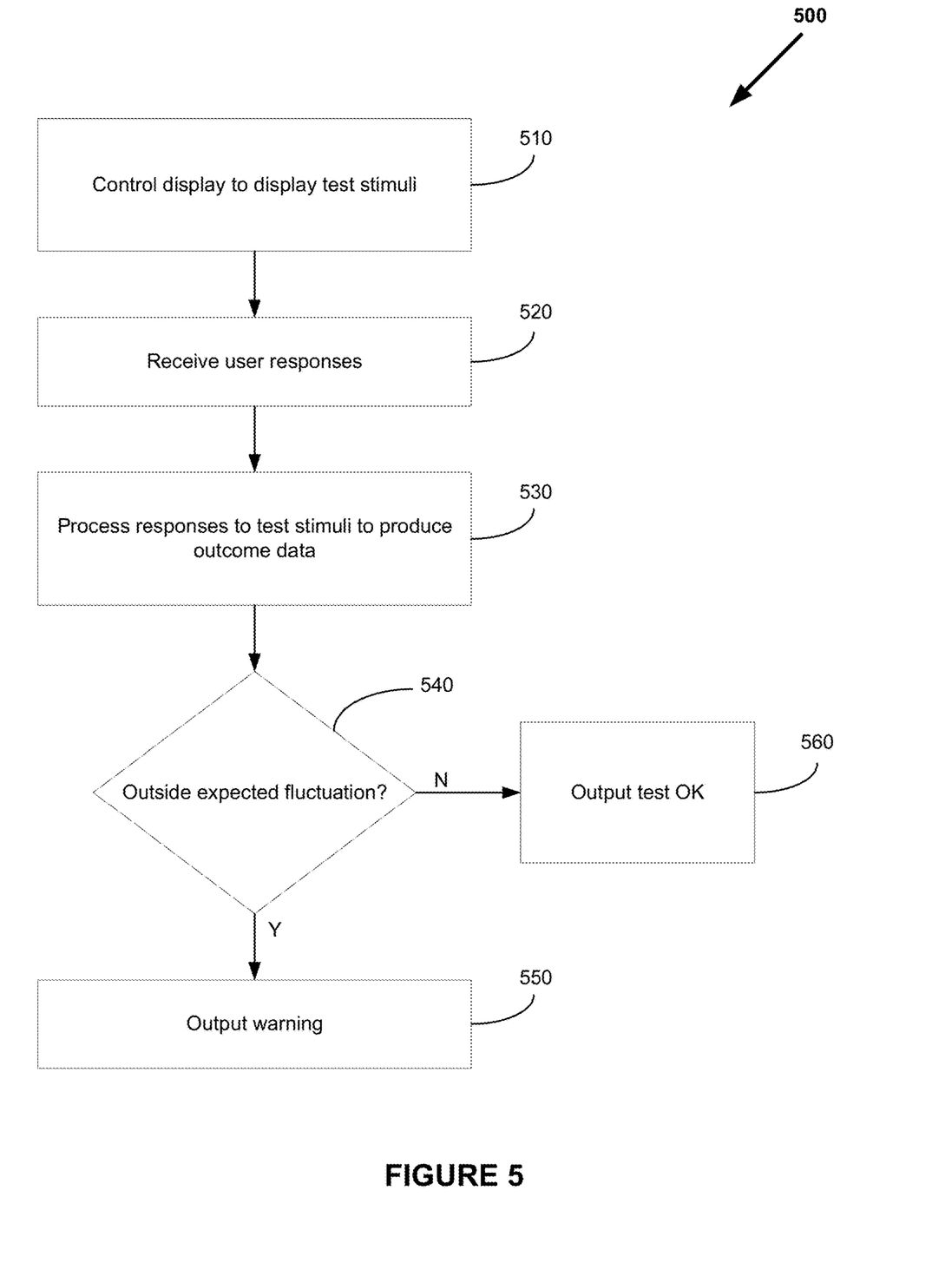
FIG. 5 shows a method according to an embodiment of the invention.

A method 500 of an embodiment of the invention is shown in FIG. 5. At step 510, the method involves controlling the display of an electronic device, such as a portable tablet device with a touch screen, to display test stimuli to the user. Embodiments of the invention involve presenting test stimuli of at least one spatial visual contextual test that is a perceptual analogue of centre-surround neuronal responses in human vision on an electronic device. That is, appropriate test stimuli include all classes of spatial visual contextual effects that are considered to be perceptual analogues of centre-surround neuronal responses in human vision. Broadly, these stimuli include patterns where there is a difference between a central target and its surround (such as the various stimuli shown in the article "Visual Contextual Effects of Orientation, Contrast, Flicker, and Luminance: All Are Affected by Normal Aging" by Bao N. Nguyen and Allison M. McKendrick, published in Frontiers in Aging Neuroscience on 18 Apr. 2016 and available at https://www.frontiersin.org/articles/10.3389/fnagi.2016.00079/full). Spatial contextual effects can also include measuring performance for tasks where there is not a clear border between the centre and surround stimulus region, but where the spatial size of the stimulus is varied. An example of those tasks in the context of migraine can be found in the article "Center-Surround Visual Motion Processing in Migraine" by Josephine Battista, David R. Badcock and Allison M. McKendrick, published in Investigative Ophthalmology & Visual Science in November 2010 and available at https://iovs.arvojournals.org/article.aspx?articleid=2127311. Human perception performance on these tasks is linked to underlying cortical neural mechanisms that are governed by the cortical balance of neural excitation versus neural inhibition.

One suitable test is the Chubb illusion (Chubb C, Sperling G, Solomon J A. "Texture interactions determine perceived contrast." Proceedings of the National Academy of Sciences. 1989; 86(23):9631-5), whereby the perceived contrast of a grating patch is reduced in the presence of a high contrast surround, due to inhibitory lateral connections and extrastriate feedback effects on the central excitatory zone (centre-surround contrast suppression). Interictally, people who experience migraine typically perceive the central grating at lower contrast (more suppressed) than non-headache controls.

At step, 520, the method involves receiving one or more user responses to the test stimuli via the electronic device. In one example, as set of possible responses are displayed on the electronic device and user responses are received by a user touching the touch screen where a selected response is displayed.

At step 530, the electronic device processes the response to the test stimuli in accordance with the selected testing method to produce outcome data.

At step 540, the electronic device determines whether the outcome data is outside an expected fluctuation in test results for the user.

In embodiments of the invention, individual calibration of visual performance is performed. Baseline performance is derived over a minimum period of 7 days of "headache free" interval. A minimum of 7 days is recommended based on pilot data in non-headache control participants collected over a 14 day window. In some examples, the calibration process could be performed on a different electronic device (for example, an identical device with the same settings) to the one the user conducts daily testing on, and, for example, be stored on a web-accessible server. In some examples, the calibration could be updated over time based on additional headache free days.

Control data is used to determine a 95% confidence limit for difference in test-scores between days (i.e. if 100 people were tested, 95 would have day-to-day fluctuation in performance less than this limit). If performance fluctuates outside of this normative range for daily performance fluctuation, then a warning can be output to the user. In some embodiments, variation to this cut-off may be applied for users that show either unusually high or low variability between tests during their headache free interval. Each time that the application is run, the participant is asked to log whether they have experienced a migraine in the past 24 hours. Such data can be used to build up an individual pattern for a user regarding their typical time-interval between exceeding normal variability and a migraine event.

In non-headache controls, 90% of the time, the daily fluctuation is less than about 20% of the average measure. Therefore, any measure that fluctuates beyond this amount is outside the typical range of controls. This is a conservative measure because some people show much less fluctuation in their daily measures than others. Indeed, some people only show about a 5% fluctuation in measures from day-to-day. Accordingly, while a fluctuation of greater than 20% can be used to trigger an alarm, it would be preferable to calibrate to an individual. As indicated above, a period of time (a minimum of a week) when migraine free is used to establish an individual's baseline headache-free performance and baseline daily fluctuation when headache free. In an example, the calibration results could be used to classify users as lower, medium and higher variability observers (i.e. people who tend to be more standard in their performance versus those that are more variable). This can then be used to set boundaries of expected fluctuation for them as an individual (also taking into account known levels of fluctuation in those without headache). Alternatively, the trigger level can be set for an individual by adding a margin (e.g. 5%) to the user's measured fluctuation (e.g. their maximum fluctuation), or by multiplying the user's measured fluctuation by a defined amount.

Accordingly, if the outcome data is outside the expected fluctuation at step 540, the electronic device controls the display to output a warning to the user 550, for example a message warning of potential migraine onset. If not, the method outputs 560 a message (e.g. "test OK") indicating that the test outcome is not indicative of a migraine onset. In other examples, the electronic device can also output the warning to one or more stored contacts.

Experimental Results

Equipment

Visual tasks were conducted using the open access application PsyPad 2.0 (Turpin A, Lawson D J, McKendrick A M. "PsyPad: A platform for visual psychophysics on the iPad". Journal of vision. 2014; 14(3):16-) on iPad 2 devices (1024× 768 pixel, 256 bits per pixel, 30 Hz, max luminance 344.5 cd/m$^2$; Apple, Calif., USA). Participants were loaned an iPad (available from Apple Inc of Cupertino, Calif.) and provided with a tape measure to perform tasks binocularly from 40 cm viewing distance. The iPads did not have other apps installed. Each iPad was set to turn "auto-brightness" off and to set screen brightness to maximum. Participants received written instructions on how to check that auto-brightness was off prior to testing, and also how to check that screen brightness was set to maximum. Participants were also shown how to check these settings during an initial visit, and compliance with this behaviour was verbally queried during a final follow-up visit.

iPads were chosen because of the availability of the device and the size of the screen, however, other electronic devices could be used.

Testing was conducted in order to monitor visual performance daily using an at-home testing protocol on an electronic device, and to compare individuals with migraine at various times in their migraine cycle, to the daily fluctuation of performance in non-headache controls. The testing measured the strength of centre surround contrast suppression (Chubb illusion).

The testing also measured luminance increment detection in spatial luminance noise. Previous studies in respect of luminance increment detection have demonstrated interictal elevation of threshold in migraine groups suggestive of an imbalance in cortical excitation and inhibition that leads to excessive neural noise. Neural noise can arise from random neural firing in the absence of a stimulus (additive noise) or due to excessive firing in response to a stimulus (multiplicative noise). By testing at high, medium and low spatial noise conditions, Webster and colleagues (Webster K E, Dickinson J E, Battista J, McKendrick A M, Badcock D R. "Evidence for increased internal noise in migraineurs for contrast and shape processing." Cephalalgia. 2012; 32(2): 125-39) revealed alterations that were interpreted by the authors as possibly arising from differences in multiplicative neural noise in their migraine group.

The inventors hypothesised that if cortical excitation increases in the lead up to a migraine and then relatively normalises post-migraine, the following patterns of performance would be observed: 1) contrast suppression should decrease immediately pre-migraine and increase post migraine; and 2) luminance increment thresholds should increase pre-migraine and decrease post migraine.

General Experimental Outline

Participants attended twice, once before and once after the at-home testing phase. At the initial session, participants were trained to use the tablet and perform the tasks. Subsequently, participants were asked to complete all parts of the daily testing without substantive breaks, at a time of day when they anticipated minimal distraction, and at approximately the same time each day. Control participants performed the daily tasks over a 14-day period. People with migraine conducted daily testing until they experienced a migraine event, and then for the following week. As part of the daily testing, migraine participants were required to indicate via a survey question embedded in the tablet app if they had experienced a migraine in the past 24 hours. If they answered "yes", the participant was contacted via telephone within the next 48 hours to confirm that the event was consistent with a typical migraine with or without aura. In an attempt to improve compliance, all participants received a thank you message (via their indicated preferred mode of contact: text message on their mobile device or email) every 3 to 7 days during the home monitoring phase. If they missed a day of testing, participants were contacted via voice call or text message on their preferred mode of contact (mobile number or email), to check if they had forgotten or had any technical issues with the tablet. They were asked to resume daily testing as soon as possible. All participants returned for a final laboratory session where they performed the tasks on the tablet once more under supervision to allow comparison between the performance measured in the initial (Lab 1) and final (Lab 2) sessions to quantify any practice effects arising from the daily home testing period. All migraine participants were headache-free and asymptomatic at the two in-office sessions. The home testing was completed in no more than 10 minutes each day. Details of the specific tests appear below.

Participants

Data was collected and analysed for sixteen non-headache controls (mean age 26.8, 19-46 years, 5 males), 10 people with migraine with aura (MA) (mean age 32.1, 19-47 years, 2 males) and 8 people with migraine without aura (MO) (mean age 33.1, 20-49 years, 1 male). An additional 3 individuals with migraine enrolled in the study but were excluded after they did not have a migraine event within 2 months of home testing. A minimum sample size of 15 controls and 15 with migraine was estimated to find between group differences during the interictal period. Migraine participants had been diagnosed with migraine by their general practitioner or neurologist and had symptoms consistent with the International Classification of Headache Disorders (ICHD)-II criteria for migraine with (MA) or without (MO) aura (Headache Classification Committee of the International Headache Society. The international classification of headache disorders, (beta version). Cephalalgia. 2013; 33(9):629-808). A clinical migraine history was recorded including the number of days since their last migraine (median; interquartile range (IQR): 7, 2-30 days), number of attacks per year (median, IQR: 19, 15-28 attacks) and symptoms required to confirm MO or MA. Impact of migraine was graded using the Migraine Disability Assessment (MIDAS) (median, IQR: 3, 1-4). Participants were required to experience migraines every 1-4 weeks to ensure that a headache-free period and at least one migraine attack could be captured within a reasonable duration of the home testing (ideally within a month). Those with chronic migraine were excluded.

Control participants had never experienced a migraine, or migraine aura. In addition, non-headache status was defined as no more than four headaches per year, with those headache events clearly explicable (for example, influenza or dehydration). All participants underwent a brief optometric screening to ensure normal vision. All had refractive errors within ±5D spherical and less than 2D cylindrical, with best corrected visual acuity of 6/7.5 or better, and normal ophthalmic health. Participants were not permitted to suffer from any other neurological conditions, nor to take regular medications known to affect vision or cognition, including migraine prophylactics.

Stimuli

Figure 1A:
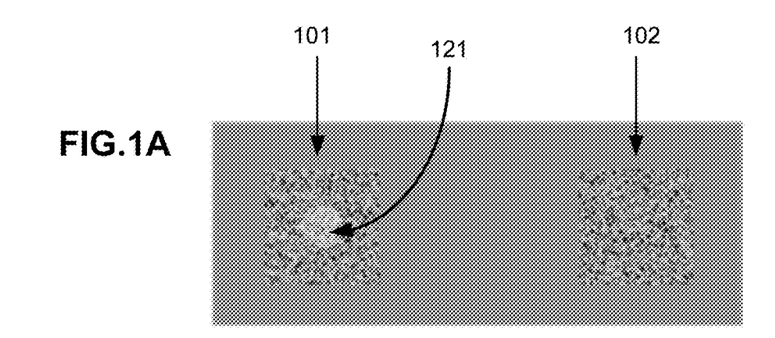
FIGS. 1A and 1B represent a luminance increment detection test stimulus in high and low spatial luminance noise respectively.
Figure 1B:
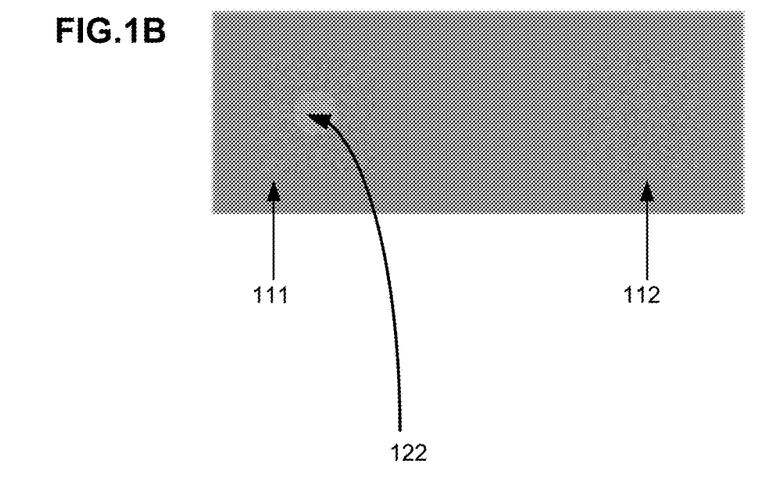

FIGS. 1A and 1B represent the luminance increment detection test stimulus in high and low spatial luminance noise respectively. In each case, two spatial luminance noise squares 101,102,111,112 (each 4 deg of visual angle) were presented with centres 5.5 deg from the screen centre, on a mean background luminance of 201 $cd/m^2$. Noise squares 101,102,111,112 were filled with noise super-pixels, each 6×6 standard pixel (0.2×0.2 deg of visual angle). The luminance noise was randomly sampled from a Gaussian distribution (mean=0; stdev=26.25 $cd/m^2$ (low noise) or 52.5 $cd/m^2$ (high noise)). One of the squares 101,102,111,112 was randomly selected to present a superimposed luminance increment (1.5 deg diameter circle) (Squares 101,102 in the illustrated example with circles 121,122). Stimuli duration was 500 ms. Participants were instructed to make a quick eye movement to view both squares before indicating whether the luminance increment appeared on the left or right. Participants indicated their response by tapping on touchscreen regions (3.4×3.4 deg of visual angle) at the bottom left corner of the display (if they were answering left) and right corner of the display (if they were answering left). The next stimulus was presented 500 ms after a response. The luminance of the circle 121,122 varied according to two interleaved 3-down-1-up staircases that each terminated after four reversals, converging on the approximate 79% correct performance level. The initial luminance was the same for both staircases, commencing at 25 $cd/m^2$ for the high noise case and 8 $cd/m^2$ for the low noise task. The initial step size was 5.4 $cd/m^2$ with the step-size halved on the first two reversals to reach a final step-size of 1.34 cd/m². Individual thresholds were calculated as the mean of the last two reversals of both staircases.

Figure 1C:
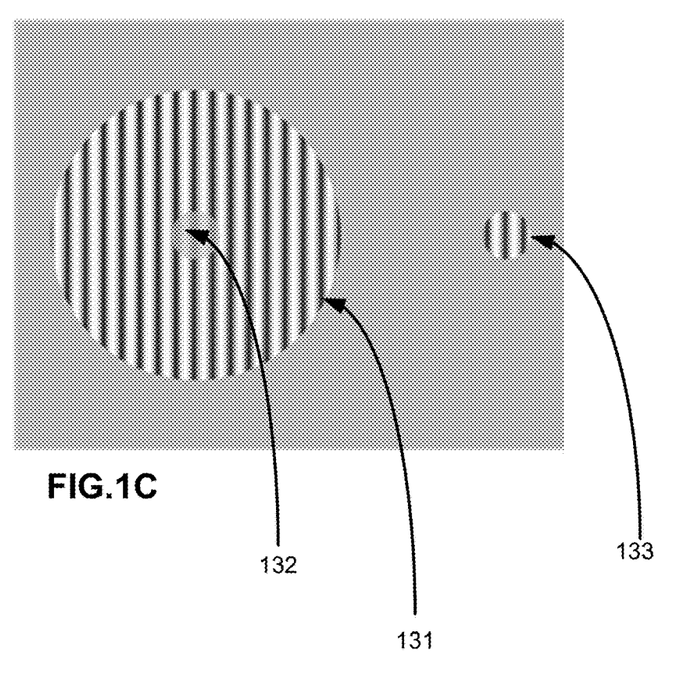
FIG. 1C shows an example centre-surround contrast test stimulus.

FIG. 10 shows the centre-surround contrast test stimulus (mean background luminance 172 cd/m²) which was a drifting sine grating (spatial frequency 2 c/deg; drift rate 2 deg/s, randomised drift direction and starting phase) in a circular envelope consisting of a central area 132 (0.67 deg radius) and a surround annulus 131 (outer circumference: 4 deg radius, inner circumference: 0.67 deg radius). The drifting grating was constructed of 8 movie frames, each presented for 66.67 ms (2 frames; total stimulus duration 533.33 ms). The contrast of the annular stimulus 131 (FIG. 10—left) was fixed at 40% centrally and 95% for the annulus (reference stimulus). For the no-surround stimulus 133 (FIG. 10—right), the central contrast varied according to two interleaved 1-down-1-up staircases designed to converge on the point of subjective equality. Both staircases commenced with a contrast of 30% and terminated after six reversals with an initial step size of 8% contrast, and subsequent steps sizes halved to reach a minimum step size of 2% contrast. Individual thresholds were calculated as the mean of the last four staircase reversals. Stimulus duration was 533 ms during which participants compared the contrast of both central gratings, before indicating the location of the higher contrast centre by tapping on lower left and right touchscreen regions (3.4×3.4 deg of visual angle). The next stimulus was presented 500 ms after a response was registered.

Stimuli were created using a customised script written in Matlab R2016b (Mathworks, Natick, Mass., United States) run on a personal computer. For each luminance noise and contrast level, ten variants, varying in noise jitter, drift direction and phase, were generated and the image sets uploaded to the PsyPad server. For each stimulus presentation, the PsyPad application randomly presented one of the ten variants to ensure stimulus properties (noise jitter, drift direction, phase) were randomised between trials.

Daily test order was fixed: 1) the migraine survey question; 2) luminance increment detection in high noise; 3) luminance increment detection in low noise and 4) centre-surround contrast discrimination. Participants were instructed to perform the daily test under the same conditions each day, including location, approximately similar time each day and to avoid screen reflections, glare and shadows. All participants were provided with a take-home instruction sheet detailing reminder to maintain consistency in test lighting.

Analysis

Headache free days were defined as more than 2 days before a migraine and more than 2 days after a migraine. Data for headache free days were pooled within an individual, as were the other timepoints (2 days pre-migraine (2M), 1 day pre-migraine (1M), migraine event (M), 1 day post-migraine (M1), 2 days post-migraine (M2)) if more than one migraine event was captured (12 participants, but most with only one attack with no missing data). When attacks lasted for more than one day (but always less than three days to fit the criteria for typical episodic migraine), data within the individual were averaged across all attack days. For controls, data for each individual was averaged across test-days, either for the first and second week of testing separately, or for the entire duration (see below for specific analyses). Missing data was ignored in the averaging process (i.e. if controls did not perform the test on all 14 days; or people with migraine did not perform the tests on all headache free days).

Statistical analyses were conducted in SPSS Statistics Version 21 (IBM, New York, USA). Group averages were compared using paired t-tests except for when normality test failed where Mann-Whitney Rank Sum Test was used. To examine changes in luminance increment detection thresholds across migraine time points, a two-way repeated measures analysis of variance (RM-ANOVA factors: noise level×timepoint) was used.

Reduced Luminance Increment Detection Thresholds in the Migraine Group for Both High and Low Noise FIG. 2 shows averaged luminance increment detection thresholds for the control (left bar in each pair of bars) and migraine (right bar in each pair of bars) groups under high luminance noise (FIG. 2A) and low noise conditions (FIG. 2B) at their initial lab session (Lab 1), final lab session post home-monitoring (Lab 2) and home-monitoring test phase (Home: note that only the individual headache-free days contributed to this measure for the migraine group). FIGS. 2A and 2B shows that luminance increment detection thresholds were higher in the high luminance noise condition than in the low noise condition (main effect of noise level: $F(1,32)=231.10$, $p<0.001$). Participants with migraine had significantly lower luminance increment detection thresholds relative to controls (main effect of group: $F(1,32)=8.49$, $p<0.01$) for both conditions (non-significant noise level× group interaction: $F(1,32)=2.860$, $p=0.101$). While the raw thresholds were reduced, the ratio of the high noise to low noise thresholds were comparable between groups (non-significant effect of group: $F(1,32)=2.97$, $p=0.09$) (FIG. 2C).

Reduced Centre-surround Perceived Contrast in the Migraineurs

Figure 2A:
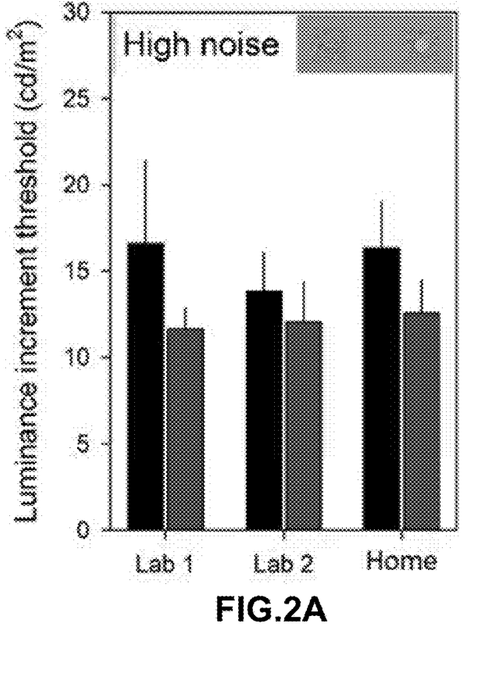
FIGS. 2A and 2B show averaged luminance increment detection thresholds for a control and migraine groups under high luminance noise and low noise conditions respectively.
Figure 2B:
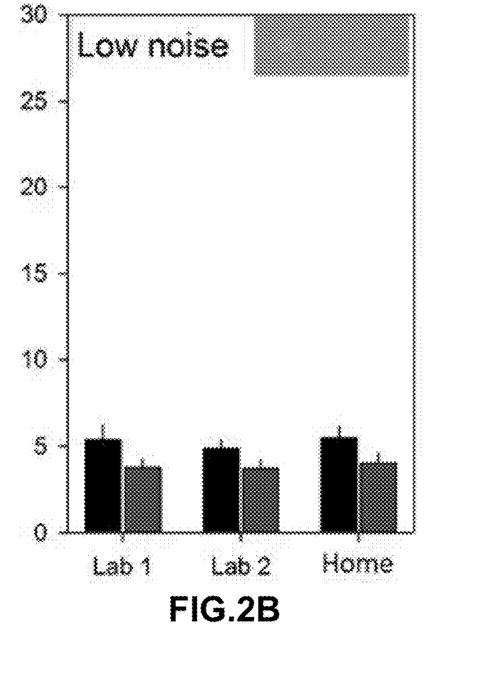
Figure 2C:
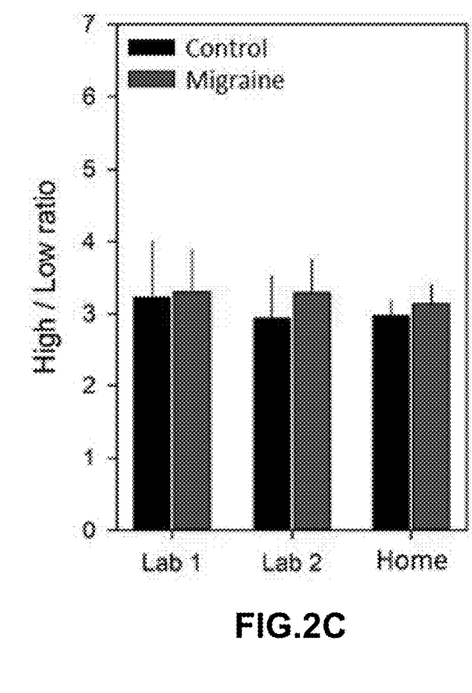
FIG. 2C shows the ratio of the high noise to low noise thresholds.
Figure 2D:
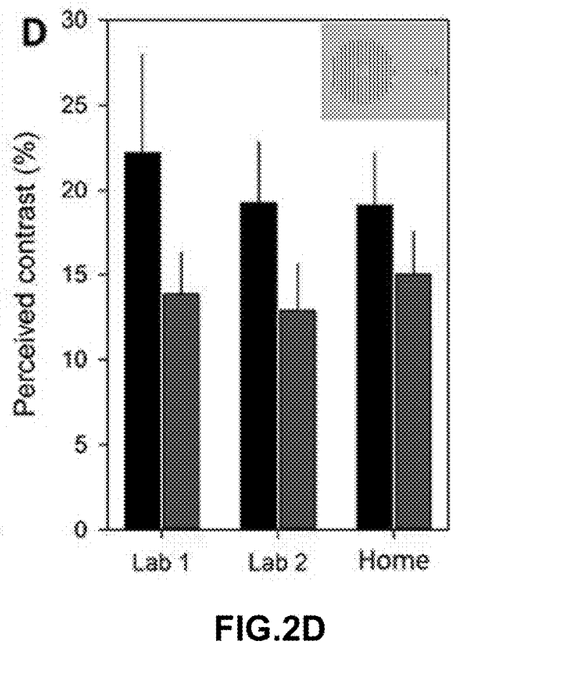
FIG. 2D shows group averaged perceived contrast in the centre-surround task.

FIG. 2D shows group averaged perceived contrast in the centre-surround task. Participants with migraine perceived the central grating at a lower contrast than the controls (more suppression) (main effect of group: $F(1,32)=9.51$, $p<0.01$). Error bars represent 95% confidence intervals of the mean.

Figure 3A:
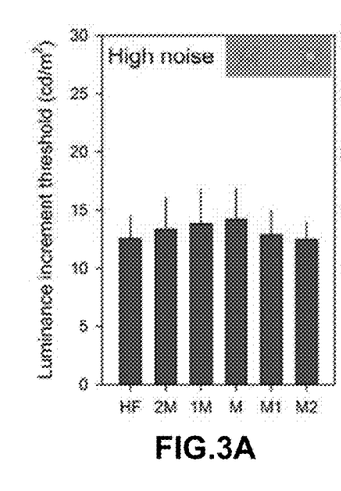
FIGS. 3A-3F depict the average luminance thresholds measured in the migraine group throughout their migraine cycle.
Figure 3B:
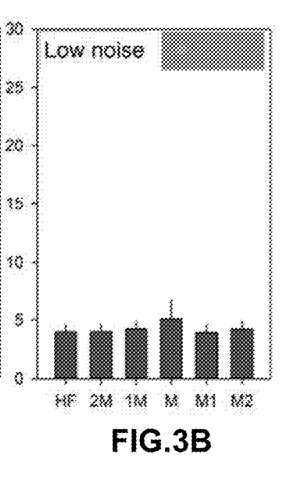
Figure 3C:
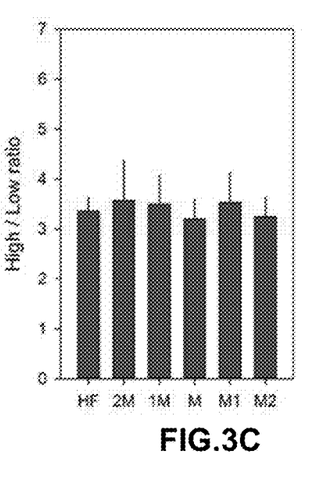
Figure 3D:
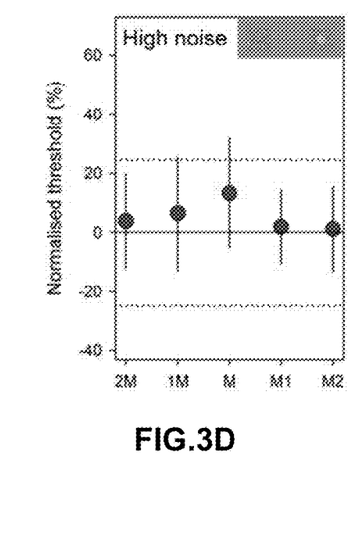
Figure 3E:
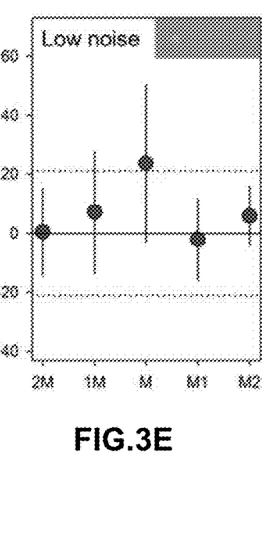
Figure 3F:
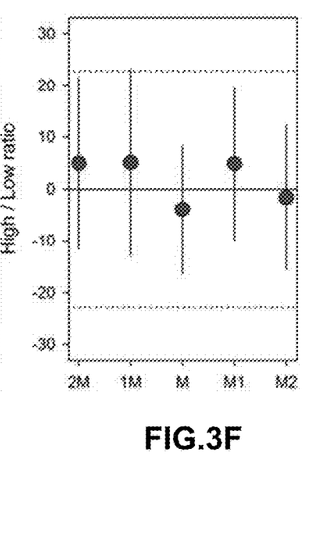

No Main Effect of Migraine Timepoint on the Luminance Increment Detection Thresholds FIGS. 3A-3F depict the average luminance thresholds measured in the migraine group throughout their migraine cycle. FIG. 3A corresponds to the high noise test and show the group averaged luminance increment detection thresholds obtained across different timepoints in the migraine cycle (HF—headache-free; 2M—two days pre-migraine; 1M—one day pre-migraine; M—attack day(s); M1—one day post-migraine; M2—two days post-migraine). FIG. 3B shows the averaged luminance increment detection threshold for low noise. For the luminance increment detection task, thresholds were higher for the high noise than low noise condition (main effect of noise level: $F(1,15)=151.69$, $p<0.001$) but not different across days for either condition (non-significant effect of timepoint: $F(5,75)=1.38$, $p=0.24$; non-significant noise×timepoint interaction: $F(5,75)=0.42$, $p=0.83$). As shown in FIG. 3C, the ratio between the threshold in the high and low noise condition was also not altered with days pre- and post-migraine (non-significant effect of timepoint: $F(5,75)=0.78$, $p=0.56$). After normalising increment detection thresholds to individual thresholds on headache-free days to account for baseline differences, as shown in FIGS. 3D to 3F (corresponding to FIGS. 3A to 3C respectively), there was still no significant change across days pre- and post-migraine (non-significant effect of timepoint: $F(4,60)=1.92$, $p=0.12$). In FIGS. 3D to 3F dotted line represents the 95% limits of group variability of the controls and error bars represent 95% confidence intervals.

Reduced Centre-Surround Suppression Two Days Pre-Migraine

Figure 4A:
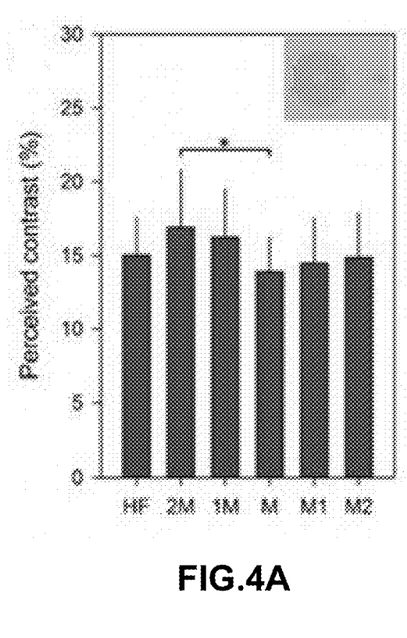
FIG. 4A shows group averaged perceived contrast thresholds obtained across different timepoints in the migraine cycle.

FIG. 4A shows group averaged perceived contrast thresholds obtained across different timepoints in the migraine cycle (HF—headache-free; 2M—two days pre-migraine; 1M—one day pre-migraine; M—attack day(s); M1—one day post-migraine; M2—two days post-migraine). Error bars represent 95% confidence intervals. From FIG. 4A it can be seen that for the centre-surround perceived contrast task, performance did alter in proximity to a migraine (main effect of timepoint: $F(5,75)=3.32$, $p<0.01$ (FIG. 4A). Post-hoc paired t-tests confirmed significantly elevated perceived contrast (reduced surround suppression) 2 days pre-migraine ($t(17)=-2.23$, $p=0.04$), and a close to significant increase in perceived contrast 1 day pre-migraine ($t(17)=-2.07$, $p=0.06$).

Figure 4B:
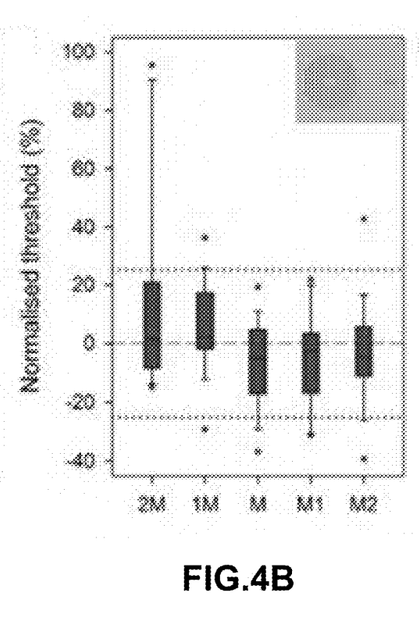
FIG. 4B shows group averaged perceived contrast thresholds normalised to individual headache-free days.

FIG. 4B shows group averaged perceived contrast thresholds normalised to individual headache-free days. Dotted line represents the group variability of the controls. Error bars represent $25^{th}$ and $75^{th}$ percentiles and symbols represent outliers. FIG. 4B demonstrates that the same group trend holds even after normalising individual perceived contrast thresholds to their own thresholds on headache-free days as a percentage change (main effect of timepoint: $F(4,60)=3.88$, $p<0.01$) (FIG. 4B). Significantly different performance as a function of timepoint is indicated by the asterisk ($p<0.05$).

In order to determine the variance between individuals with respect to the day where the least contrast suppression (highest perceived contrast thresholds) was measured, the data was examined for all individuals to determine the day where they showed the least suppression (FIG. 4C), out of all days tested (note, no participants showed lowest suppression during the headache free period). There was some variance between individuals however majority of the participants demonstrated the least suppression pre- or immediately post migraine period.

Discussion

Through perceptual testing at home, the experimental data shows on average difference in centre-surround contrast suppression in the days pre- and post-migraine (FIG. 4A, 4B). Relative to headache-free baseline, the centre surround suppression was weakened (less suppression) at around 48 hours prior to a migraine and was similar to baseline by 24 hours post-migraine. Luminance increment detection thresholds remained unchanged during the migraine event period.

Figure 4C:
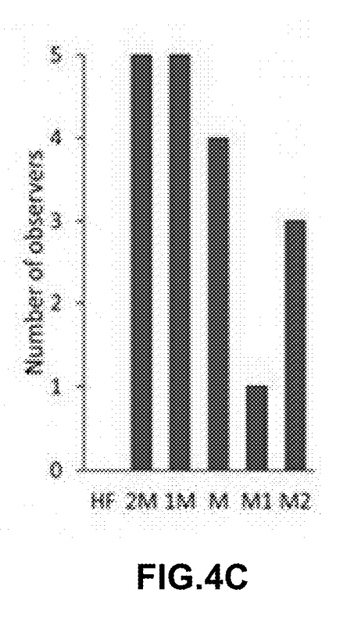
FIG. 4C shows the day on which participants demonstrated the least suppression.

While 14 of 18 (78%) of our migraine participants demonstrated reduced suppression during migraine build-up, the specific day of least suppression varied (FIG. 4C).

Centre-surround contrast suppression provides an indirect measure of the visual cortical balance in inhibition and excitation. On average, our migraine group perceived the central grating at a lower contrast than the controls (more suppression) on headache-free days (FIG. 2D). Further, the daily testing data, shows that surround suppression is weakened (higher perceived contrast) at around 48 hours prior to a migraine attack and strengthened to approach their headache-free baseline (lower perceived contrast) by 24 hours post-migraine (FIG. 4A, 4B). The precise neuroanatomical mechanisms driving these centre-surround contrast changes likely involves an interdependent neurotransmitter cascade. Performance on perceptual centre-surround suppression tasks has been correlated with levels of GABA concentration in human visual cortex as measured by magnetic resonance spectroscopy, in addition to influenced by dysregulation of cholinergic mechanisms. A plausible interpretation is that the balance between cortical inhibition and excitation swings towards excessive excitation (reduced inhibition and therefore reduced perceptual suppression) in the immediate pre-migraine phase, relatively normalises immediately post-migraine (increasing perceptual contrast suppression), and then tips towards an excessive inhibitory state in the interictal phase (more perceptual contrast suppression than controls).

The luminance increment detection task was included because task performance is predicted to change if internal neural noise alters in proximity to a migraine. Previous work reported elevated thresholds in migraine relative to controls that were interpreted as consistent with a model of increased multiplicative neural noise during the interictal phase using a variant of this stimulus. Consequently, we hypothesised that luminance detection thresholds would be elevated in proximity to a migraine event (consistent with increased excitatory neural noise). Our data did not support this hypothesis. FIG. 3 suggests somewhat poorer performance on the day of the migraine, however, this was not statistically significant.

The invention claimed is:

1. A method of outputting a warning indicative of potential migraine onset comprising:
   controlling a display of an electronic device to display, to a user, test stimuli of at least one spatial visual contextual test that is a perceptual analogue of centre-surround neuronal responses in human vision;
   receiving, via an input device of the electronic device, at least one response of the user to the test stimuli;
   processing the at least one response of the user to obtain test outcome data; and
   outputting a warning indication of potential migraine onset to the user if the test outcome data is outside an expected range for daily fluctuation in test outcome data.

2. The method of claim 1, comprising comparing the test outcome data to base line data for the user obtained during a migraine headache free period to determine whether the fluctuation in test outcome data is outside the expected range for daily fluctuation in test outcome data.

3. The method of claim 2, comprising setting a value for determining whether test outcome data for a user is outside the expected range for daily fluctuation in test outcome data based on the base line data for the user obtained during a migraine headache free period.

4. The method of claim 2, comprising setting a value for determining whether test outcome data for a user is outside the expected range for daily fluctuation in test outcome data based on measures of fluctuation obtained for a plurality of users.

5. A non-transitory computer readable medium comprising computer program instructions which when executed by a processor of an electronic device, implements a method of outputting a warning indicative of potential migraine onset comprising:
   controlling a display of the electronic device to display, to a user, test stimuli of at least one spatial visual contextual test that is a perceptual analogue of centre-surround neuronal responses in human vision;
   receiving, via an input device of the electronic device, at least one response of the user to the test stimuli;
   processing the at least one response of the user to obtain test outcome data; and
   outputting a warning indication of potential migraine onset to the user if the test outcome data is outside an expected range for daily fluctuation in test outcome data.

6. The non-transitory computer readable medium of claim 5, wherein when the instructions are executed they cause the processor to compare the test outcome data to base line data for the user obtained during a migraine headache free period to determine whether the fluctuation in test outcome data is outside the expected range for daily fluctuation in test outcome data.

7. The non-transitory computer readable medium of claim 6, wherein when the instructions are executed they cause the processor to set a value for determining whether test outcome data for a user is outside the expected range for daily fluctuation in test outcome data based on the base line data for the user obtained during a migraine headache free period.

8. The non-transitory computer readable medium of claim 6, wherein when the instructions are executed they cause the processor to set a value for determining whether test outcome data for a user is outside the expected range for daily fluctuation in test outcome data based on measures of fluctuation obtained for a plurality of users.

* * * * *